US010616457B2

(12) United States Patent
Fletcher et al.

(10) Patent No.: US 10,616,457 B2
(45) Date of Patent: Apr. 7, 2020

(54) CELLSCOPE APPARATUS AND METHODS FOR IMAGING

(71) Applicant: THE REGENTS OF THE UNIVERSITY OF CALIFORNIA, Oakland, CA (US)

(72) Inventors: Daniel Fletcher, Berkeley, CA (US); Erik Douglas, Oakland, CA (US); Amy Sheng, San Francisco, CA (US); Wilbur Lam, Decatur, GA (US); Robi Maamari, Pittsburgh, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 73 days.

(21) Appl. No.: 15/403,874

(22) Filed: Jan. 11, 2017

(65) Prior Publication Data

US 2017/0126943 A1    May 4, 2017

Related U.S. Application Data

(60) Continuation of application No. 15/052,347, filed on Feb. 24, 2016, which is a continuation of application (Continued)

(51) Int. Cl.
*H04N 5/225* (2006.01)
*G02B 25/00* (2006.01)
(Continued)

(52) U.S. Cl.
CPC ....... *H04N 5/2254* (2013.01); *A61B 1/00108* (2013.01); *A61B 1/04* (2013.01);
(Continued)

(58) Field of Classification Search
CPC ........ G02B 7/027; G02B 7/14; G02B 25/002; H04N 5/2254; H04N 5/2256;
(Continued)

(56) References Cited

U.S. PATENT DOCUMENTS 5,202,758 A    4/1993   Tamburrino
5,982,559 A    11/1999  Furutake
(Continued)

FOREIGN PATENT DOCUMENTS

CN    2722826Y B    9/2005
CN    101212926 A   7/2008
(Continued)

OTHER PUBLICATIONS

Korean Intellectual Property Office, International Search Report and Written Opinion dated May 15, 2012 for related PCT International Patent No. PCT/US2011/058466 (pp. 1-9) with claims searched (pp. 10-18) pp. 1-18.
(Continued)

*Primary Examiner* — Michael S Osinski
(74) *Attorney, Agent, or Firm* — O'Banion & Ritchey LLP; John P. O'Banion

(57) ABSTRACT

An improved system and methods for enhancing the imaging of cameras included with wireless mobile devices, such as cellular phone or tablets. The imaging system includes a releasable optical attachment for imaging skin surfaces and cavities of the body. The releasable optical attachment comprises optical enhancement elements such as magnifying lenses, illumination diverting elements, and filters. Images can be viewed and analyzed on the mobile device, or transmitted to another location/device for analysis by a person or software. The results can be used to provide diagnosis, or for a variety of other applications including image comparison over time and product recommendations.

15 Claims, 10 Drawing Sheets

Related U.S. Application Data

No. 13/855,501, filed on Apr. 2, 2013, now Pat. No. 9,325,884, application No. 15/403,874, which is a division of application No. 13/855,501, which is a continuation of application No. PCT/US2011/058466, filed on Oct. 28, 2011.

(60) Provisional application No. 61/532,617, filed on Sep. 9, 2011, provisional application No. 61/408,568, filed on Oct. 29, 2010.

(51) Int. Cl.
| | | |
|---|---|---|
| *H04M 1/21* | (2006.01) | |
| *H04N 17/00* | (2006.01) | |
| *A61B 1/00* | (2006.01) | |
| *A61B 1/04* | (2006.01) | |
| *A61B 1/227* | (2006.01) | |
| *A61B 5/00* | (2006.01) | |

(52) U.S. Cl.
CPC ............ *A61B 1/227* (2013.01); *A61B 5/0077* (2013.01); *G02B 25/002* (2013.01); *H04M 1/21* (2013.01); *H04N 5/2257* (2013.01); *H04N 17/002* (2013.01)

(58) Field of Classification Search
CPC ............... H04N 5/2257; H04N 17/002; A61B 1/00108; A61B 1/04; A61B 1/227; H04M 1/21
See application file for complete search history.

(56) References Cited

U.S. PATENT DOCUMENTS

| | | | |
|---|---|---|---|
| 6,549,653 B1 * | 4/2003 | Osawa | H04N 1/60 358/504 |
| 6,606,413 B1 | 8/2003 | Zeineh | |
| 6,950,241 B1 | 9/2005 | Liang | |
| 6,961,086 B1 * | 11/2005 | Ichikawa | H04N 5/2251 348/188 |
| 7,821,569 B2 | 10/2010 | Yang | |
| 8,743,194 B2 | 6/2014 | Fletcher et al. | |
| 8,786,695 B2 | 7/2014 | Fletcher et al. | |
| 9,137,466 B2 * | 9/2015 | Ovsiannikov | H04N 5/3655 |
| 9,154,594 B2 | 10/2015 | Fletcher et al. | |
| 9,325,884 B2 | 4/2016 | Fletcher et al. | |
| 9,523,845 B2 | 12/2016 | Fletcher et al. | |
| 2003/0078517 A1 | 4/2003 | Kensey | |
| 2003/0103262 A1 | 6/2003 | Descour et al. | |
| 2003/0164895 A1 | 9/2003 | Vilnikanoja et al. | |
| 2004/0032982 A1 * | 2/2004 | Nishizawa | G09G 3/2007 382/171 |
| 2004/0062545 A1 | 4/2004 | Ushiro | |
| 2004/0239795 A1 * | 12/2004 | Kitajima | H04N 5/23212 348/362 |
| 2005/0001144 A1 | 1/2005 | Cartlidge | |
| 2005/0063605 A1 * | 3/2005 | Huang | G06K 9/00248 382/260 |
| 2005/0135665 A1 * | 6/2005 | Shinbata | G06T 5/004 382/132 |
| 2005/0266839 A1 | 12/2005 | Paul | |
| 2005/0270401 A1 * | 12/2005 | Hatano | H04N 5/2254 348/335 |
| 2006/0222567 A1 | 10/2006 | Kloepfer | |
| 2006/0233545 A1 | 10/2006 | Senba et al. | |
| 2006/0291842 A1 | 12/2006 | Tokiwa et al. | |
| 2007/0183930 A1 | 8/2007 | Roman | |
| 2007/0196019 A1 * | 8/2007 | Yamaguchi | G06K 9/00288 382/224 |
| 2007/0262236 A1 * | 11/2007 | Pertsel | H04N 5/2354 250/208.1 |
| 2007/0280677 A1 | 12/2007 | Drake | |
| 2008/0058629 A1 | 3/2008 | Seibel | |
| 2008/0207996 A1 | 8/2008 | Tsai | |
| 2009/0135287 A1 | 5/2009 | Yang | |
| 2009/0185191 A1 | 7/2009 | Boppart et al. | |
| 2009/0190822 A1 | 7/2009 | Ortyn et al. | |
| 2010/0033587 A1 | 2/2010 | Yumiki | |
| 2010/0042004 A1 | 2/2010 | Dhawan | |
| 2010/0056928 A1 | 3/2010 | Zuzak et al. | |
| 2010/0066892 A1 | 3/2010 | Momoki | |
| 2010/0098317 A1 * | 4/2010 | Kiyuna | G06T 7/0012 382/133 |
| 2010/0201809 A1 * | 8/2010 | Oyama | G01C 3/14 348/135 |
| 2011/0009163 A1 | 1/2011 | Fletcher et al. | |
| 2011/0069161 A1 * | 3/2011 | Ozawa | A61B 1/0638 348/68 |
| 2011/0069189 A1 * | 3/2011 | Venkataraman | H01L 27/14618 348/218.1 |
| 2011/0123101 A1 * | 5/2011 | Lipowezki | G01J 1/18 382/159 |
| 2011/0181947 A1 | 7/2011 | Yang | |
| 2011/0295062 A1 * | 12/2011 | Gratacos Solsona | A61B 1/00009 600/109 |
| 2012/0039593 A1 | 2/2012 | Yang | |
| 2012/0069219 A1 * | 3/2012 | Ono | H04N 9/045 348/234 |
| 2012/0133825 A1 | 5/2012 | Nakajima et al. | |
| 2012/0236424 A1 | 9/2012 | Yang | |
| 2012/0320340 A1 | 12/2012 | Coleman, III | |
| 2013/0083168 A1 * | 4/2013 | Kim | H04N 13/0239 348/47 |
| 2013/0083185 A1 | 4/2013 | Coleman, III | |
| 2013/0222562 A1 | 8/2013 | Ono | |
| 2014/0071547 A1 | 3/2014 | O'Neill et al. | |
| 2014/0078320 A1 * | 3/2014 | Hong | H04N 5/217 348/208.1 |
| 2015/0002950 A1 | 1/2015 | O'Neill et al. | |
| 2015/0042877 A1 | 2/2015 | O'Neill et al. | |
| 2015/0070557 A1 | 3/2015 | Petty et al. | |
| 2015/0172522 A1 | 6/2015 | O'Neill et al. | |

FOREIGN PATENT DOCUMENTS

| | | |
|---|---|---|
| CN | 101952762 B | 11/2012 |
| JP | H0314638 U | 2/1991 |
| JP | 2004279733 A | 10/2004 |
| KR | 10-2005-0006623 A | 1/2005 |
| KR | 10-2005-0093291 A | 9/2005 |
| KR | 10-2005-0100745 A | 10/2005 |
| TW | M385006 U | 7/2010 |
| WO | 2004/081653 A1 | 9/2004 |
| WO | 2005016135 A1 | 2/2005 |
| WO | 2005016135 A1 | 2/2005 |
| WO | 2006-083081 A1 | 8/2006 |
| WO | 2006/130967 A1 | 12/2006 |
| WO | 2009088930 A2 | 7/2009 |
| WO | 2010019515 A2 | 2/2010 |
| WO | 2012058641 A2 | 5/2012 |

OTHER PUBLICATIONS

Rodriguez, W.R. et al.—"A Microchip CD4 Counting Method for HIV Monitoring in Resource-Poor Settings"—PLoS Medicine, vol. 2, issue 7, Jul. 2005, pp. 0663-0672.

Makinen, J. et al.—"Add-on laser reading device for a camera phone"—Optical Design and Engineering II, Proc. of SPIE vol. 5962, 2005, pp. 596228-1-596228-11.

Blaivas, M. et al.—"Ultrasound image transmission via camera phones for overreading"—Amer. Journ. of Emergency Medicine—vol. 23, 2005, p. 433-438.

Frean, J.—"Microscopic images transmitted by mobile cameraphone"—Trans. of the Royal Society of Tropical Medicine and Hygiene, vol. 101, 2007, pp. 1053.

Razdan, S. et al.—"The Camera Phone: A Novel Aid in Urologic Practice"—Urology, vol. 67, issue 4, Apr. 2006, pp. 665-669.

(56) References Cited

OTHER PUBLICATIONS

Dziadzio, M. et al.—"A still image of a transient rash captured by a mobile phone"—Clinical Rheumatology, vol. 26, 2007, pp. 979-980.

Korean Intellectual Property Office, International Search Report and Written Opinion dated Aug. 19, 2009, related PCT International Application No. PCT/US08/88646 (pp. 1-5) including claims searched (pp. 6-10), pp. 1-10.

Frean, J.—"Microscopic images transmitted by mobile cameraphone"—Trans. of the Royal Society of Tropical Medicine and Hygiene, vol. 101, Jul. 30, 2007, pp. 1053.

State Intellectual Property Office of P.R.C., Notification of the First Office Action and First Office Action (translation) dated Jul. 25, 2011, related Chinese Patent Application No. 200880123463.X, translation (pp. 1-7), claims (pp. 8-12), original Chinese language version (pp. 13-15).

European Patent Office (EPO) Extended Supplemental Search Report (ESSR) dated Apr. 17, 2015 for related European Patent Application No. 11 837 229.1 (pp. 1-7) with claims searched (pp. 8-11) pp. 1-11.

State Intellectual Property Office of P.R.C., First Office Action dated Nov. 10, 2015, related Chinese Patent Application No. 201180051600.5 (pp. 1-11) with claims examined (pp. 12-16), pp. 1-16.

European Patent Office, Communication Pursuant to Rule 114(2) EPC, related EP application No. 11837229.1, dated Jan. 29, 2016, with third party communication under Article 115, pp. 1-12.

European Patent Office (EPO), Office Action dated May 9, 2016, related EP Application No. 11837229.1, pp. 1-8, with claims examined, pp. 9-14.

CellScope, "CellScope Launches iPhone Device for Diagnosing Ear Infections, Expands Telemedicine Market", Jul. 5, 2011, pp. 1-5, XP055241697.

European Patent Office (EPO), Summons to attend oral proceedings pursuant to Rule 115(1) EPC, dated Feb. 3, 2017, pp. 1-5, with claims examined, pp. 6-11.

Intellectual Property India, Examination Report dated Jul. 31, 2018, related India patent application No. 2765/CHENP/2013, pp. 1-6, claims examined, pp. 7-15.

\* cited by examiner

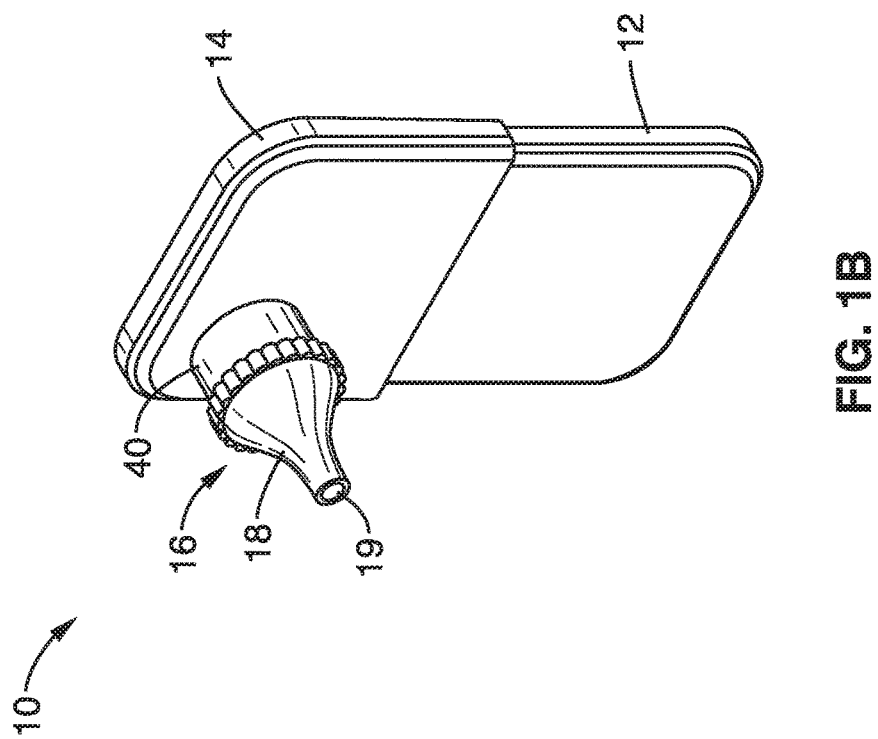
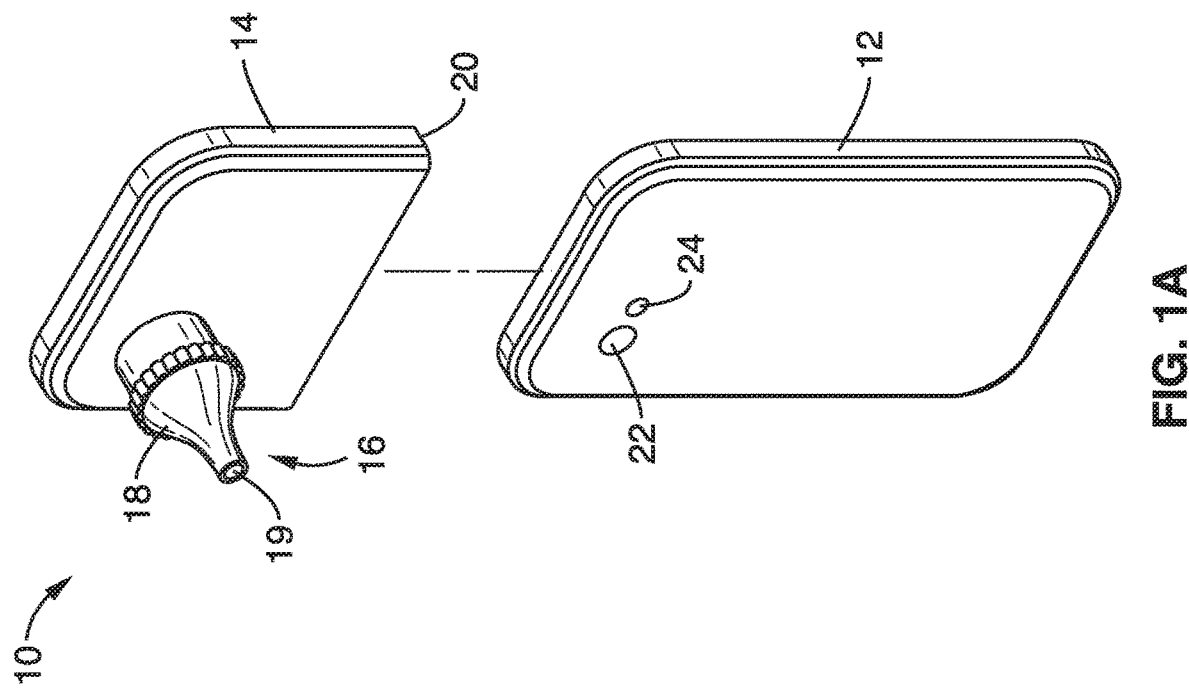

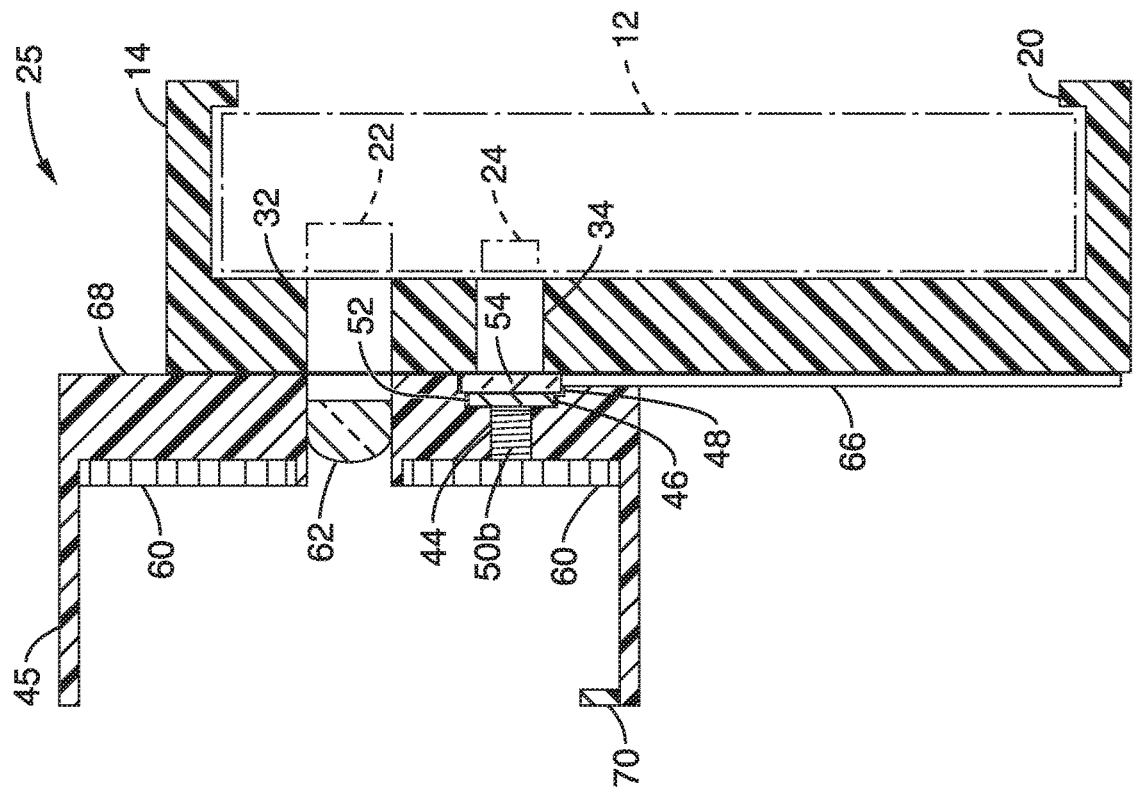
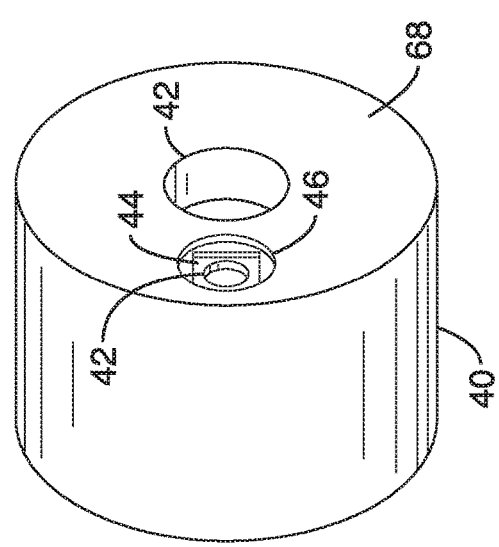
FIG. 8
FIG. 7

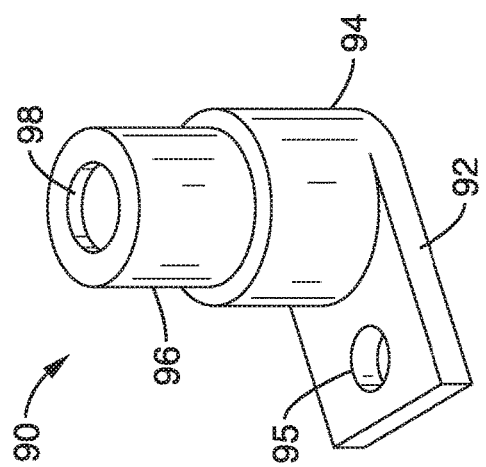
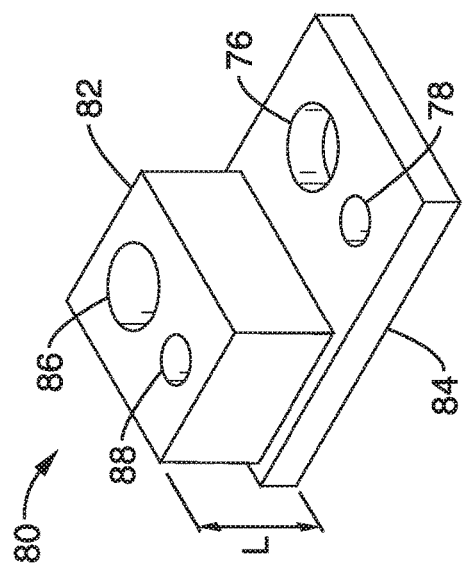
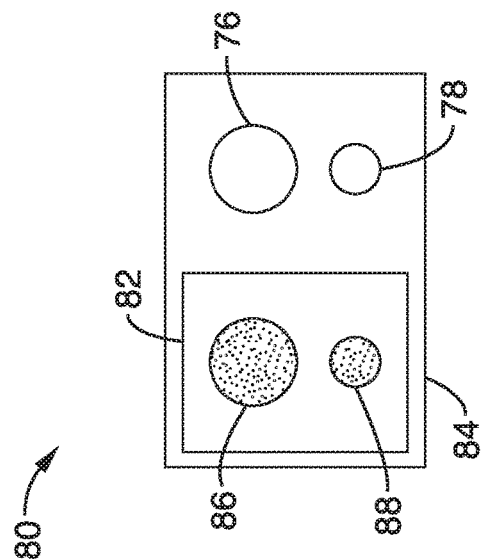
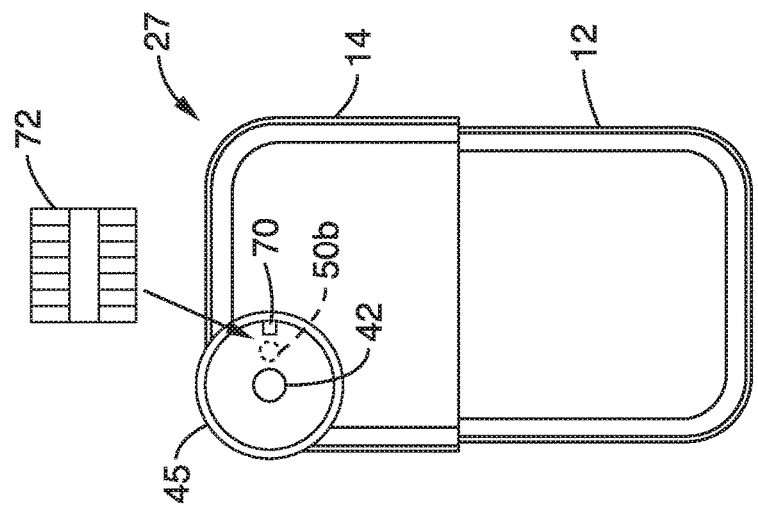

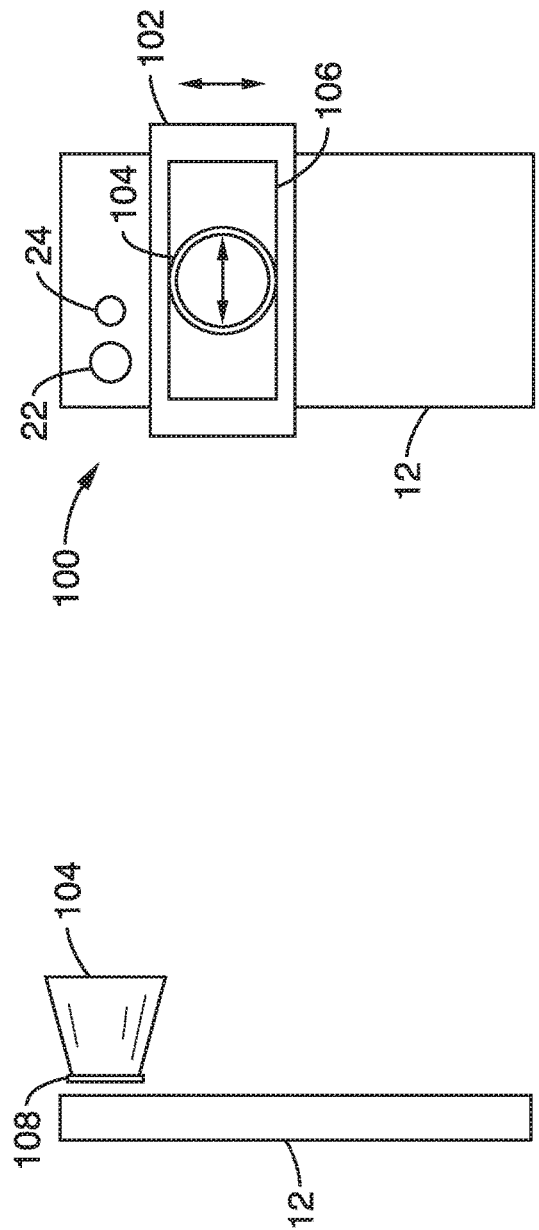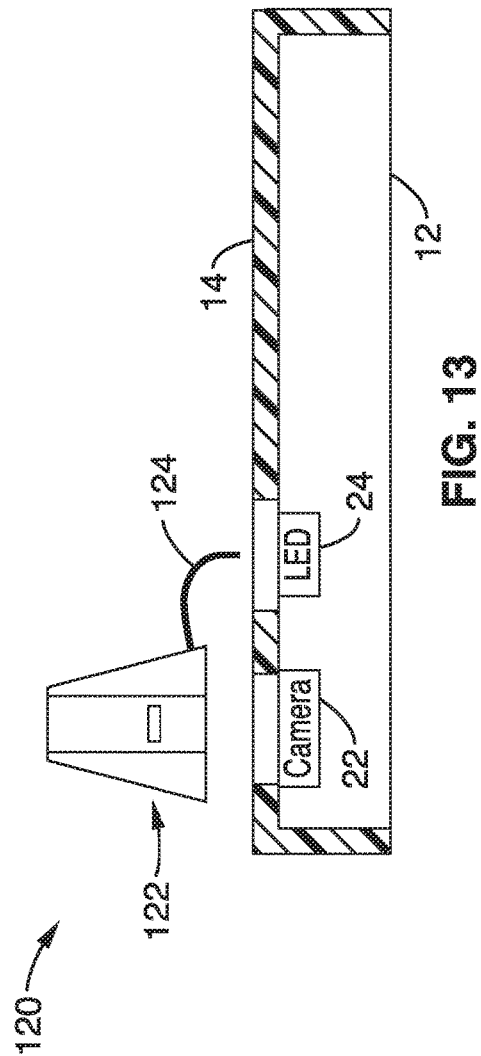

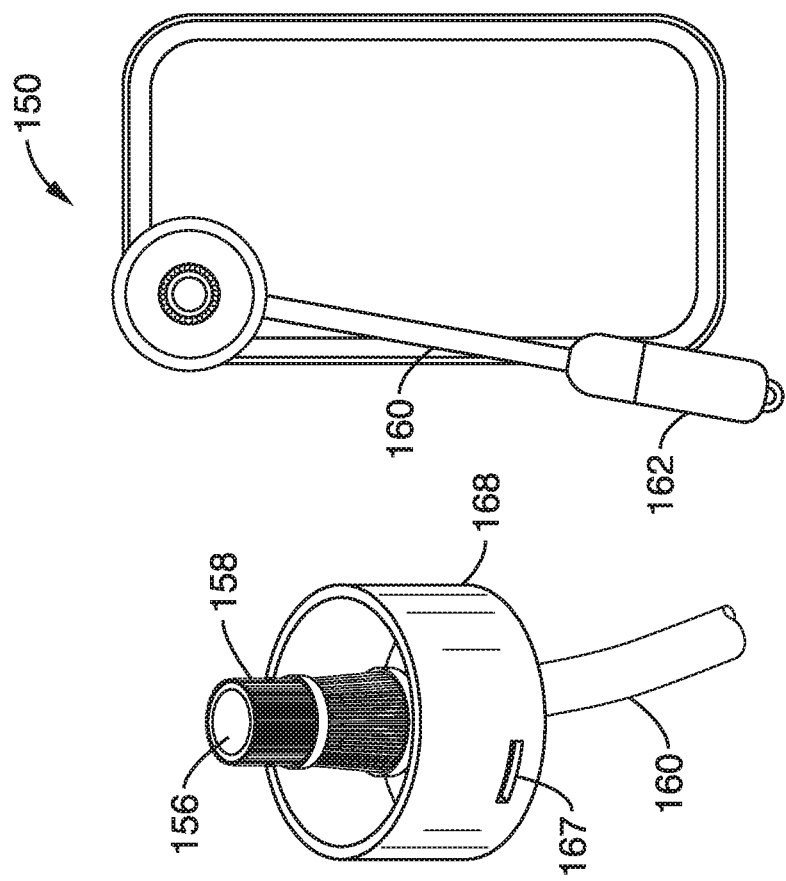
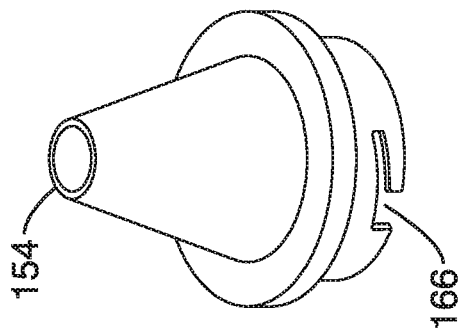
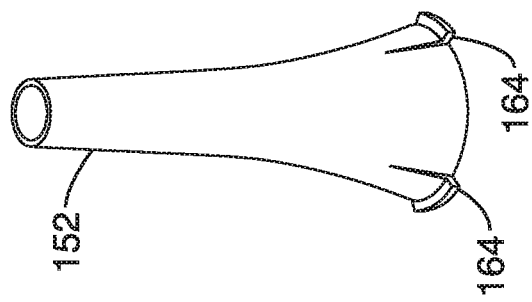
FIG. 14

CELLSCOPE APPARATUS AND METHODS FOR IMAGING

CROSS-REFERENCE TO RELATED APPLICATIONS

This application is a continuation of U.S. patent application Ser. No. 15/052,347 filed on Feb. 24, 2016, incorporated herein by reference in its entirety, which is a continuation of U.S. patent application Ser. No. 13/855,501 filed on Apr. 2, 2013, now U.S. Pat. No. 9,325,884, incorporated herein by reference in its entirety, which is a 35 U.S.C. § 111(a) continuation of PCT international application number PCT/US2011/058466 filed on Oct. 28, 2011, incorporated herein by reference in its entirety, which claims priority to and the benefit of U.S. provisional patent application Ser. No. 61/532,617 filed on Sep. 9, 2011, incorporated herein by reference in its entirety, and which claims priority to and the benefit of U.S. provisional patent application Ser. No. 61/408,568 filed on Oct. 29, 2010, incorporated herein by reference in its entirety. This application is also a division of U.S. patent application Ser. No. 13/855,501 filed on Apr. 2, 2013, now U.S. Pat. No. 9,325,884, incorporated herein by reference in its entirety. Priority is claimed to each of the foregoing applications.

The above-referenced PCT international application was published as PCT International Publication No. WO 2012/058641 on May 3, 2012 and republished on Jul. 5, 2012, and is incorporated herein by reference in its entirety.

This application is related to U.S. patent application Ser. No. 12/826,375 filed on Jun. 29, 2010, now U.S. Pat. No. 8,743,194, incorporated herein by reference in its entirety, which claims priority from, and is a 35 U.S.C. § 111(a) continuation of, PCT international application number PCT/US2008/088646 filed on Dec. 31, 2008, incorporated herein by reference in its entirety, which claims priority from U.S. provisional application Ser. No. 61/018,537 filed on Jan. 2, 2008, incorporated herein by reference in its entirety.

This application is also related to PCT International Publication No. WO 2009/088930 published on Jul. 16, 2009, incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to imaging devices, and more particularly to devices and methods for enhanced imaging with mobile electronics devices.

2. Description of Related Art

Handheld mobile devices, such as cellular phones, tablets, PDA's, etc., are becoming increasingly useful for imaging due to their ready availability to communicate with other devices wirelessly. However, the cameras and illumination sources included with most mobile electronic devices are primitive with respect to the type of imaging that may be required for special surfaces such as a patient's skin or body passage.

Many common medical tests may be performed using telemedicine, but stand-alone devices used by physicians are often too expensive or specialized to appeal to consumers.

Accordingly, an object of the present invention is an apparatus that allows mobile devices to perform as enhanced camera's and telemedicine tools, utilizing their familiar interface and ease of image capture and transmission. At least some of these objectives will be met in the description below.

BRIEF SUMMARY OF THE INVENTION

The present invention is an improved system and method for enhanced imaging using wireless transmission devices with a camera (such as a mobile phone) combined with an optical attachment. Images can be viewed and analyzed on the mobile device, or transmitted to another location/device for analysis by a person or software. The results may be used to provide diagnosis, or for a variety of other applications including image comparison over time and product recommendations.

One aspect of the invention is an imaging apparatus for a portable wireless device having a built-in camera. The apparatus includes a releasable optical assembly having a housing comprising an attachment surface for releasably coupling the releasable optical assembly to the portable wireless device, and an optical transmission element. The optical transmission element is configured to enhance an image taken by the built-in camera prior to the image being received the portable wireless device.

Another aspect is a system for enhancing and post-processing images obtained from a portable wireless device having a built-in camera, comprising: a releasable optical assembly, comprising: a housing comprising an attachment surface for releasably coupling the releasable optical assembly to the portable wireless device, and an optical transmission element. The optical transmission element is configured to enhance an image taken by the built-in camera prior to the image being received the portable wireless device. The system further comprises programming executable on said wireless device or other external device for receiving the enhanced image and post processing the enhanced image.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1A is a view of the imaging apparatus of the present invention positioned adjacent mobile device.

FIG. 1B shows the imaging apparatus of FIG. 1A installed on a mobile device in accordance with the present invention.

FIG. 7 shows a rear view of the housing of the imaging apparatus of FIG. 4.

FIG. 8 shows a cross-sectional view of the imaging apparatus of FIG. 5 installed on a mobile device in accordance with the present invention.

FIG. 9 shows the imaging apparatus of FIG. 5 with calibration module in accordance with the present invention.

FIGS. 10A and 10B show perspective and plan views, respectively, of an exposure calibration tool according to the present invention.

FIG. 11 shows a perspective view of a focus calibration tool according to the present invention.

FIG. 12A illustrates a side view of an embodiment for coupling the optical attachment of the present invention.

FIG. 12B illustrates a plan view of an alternative embodiment for coupling for the optical attachment of the present invention.

FIG. 13 shows a side view of an embodiment of a modular imaging system comprising components for imaging and illumination according to the invention.

FIG. 14 shows embodiments of a modular attachment system according to the present invention.

DETAILED DESCRIPTION OF THE INVENTION

Figure 3:
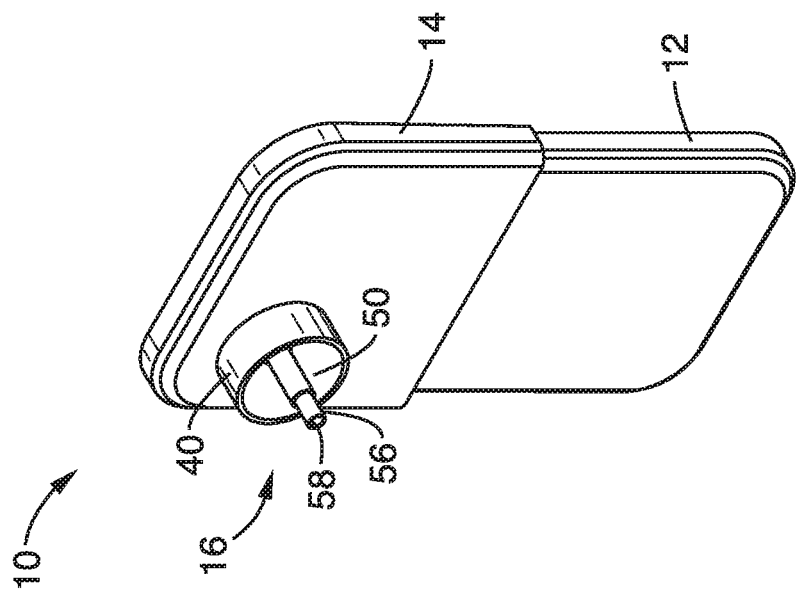
FIG. 3 shows the imaging apparatus of FIG. 1A installed on a mobile device in accordance with the present invention, with outer speculum removed for clarity.

Referring more particularly to the figures, the present invention can be embodied in various ways.

FIG. 1A illustrates a perspective view of an imaging apparatus 10 positioned adjacent handheld mobile electronic device 12. Mobile device 12 is illustrated as an iPhone 4 in the various figures depicted herein. However, it is appreciated mobile device 12 may be any wireless-enabled device having a camera, i.e. mobile device 12 may comprise any number of possible makes of cellular phones, PDA's, tablets, etc.

FIG. 1B shows the imaging apparatus 10 installed on the mobile device 12 in accordance with the present invention. Imaging apparatus 10 includes one or more optical transmission elements (e.g. lens, fiber optics, etc.) that are configured to enhance an image received by a camera 22 of device 12 prior to that image being received by the camera 22 CCD (not shown). The optical transmission elements may provide magnification and/or improved illumination to the imaged target, in addition to other imaging enhancements.

Imaging apparatus 10 includes a base member 14 that can be coupled to the mobile device 12. FIGS. 1A and 1B illustrate "clip-on" coupling means or surface 20, although other removable means such as slide-on, snap-on, or adhesives/adhesive backings are also contemplated. While base member 14 is shown in the current figures as a partial cover of the mobile device 12, base member 14 may also comprise a full case or cover (i.e. extending along the length of phone 12) that covers one or more surfaces, and releasably couples to the mobile device 12.

Figure 4:
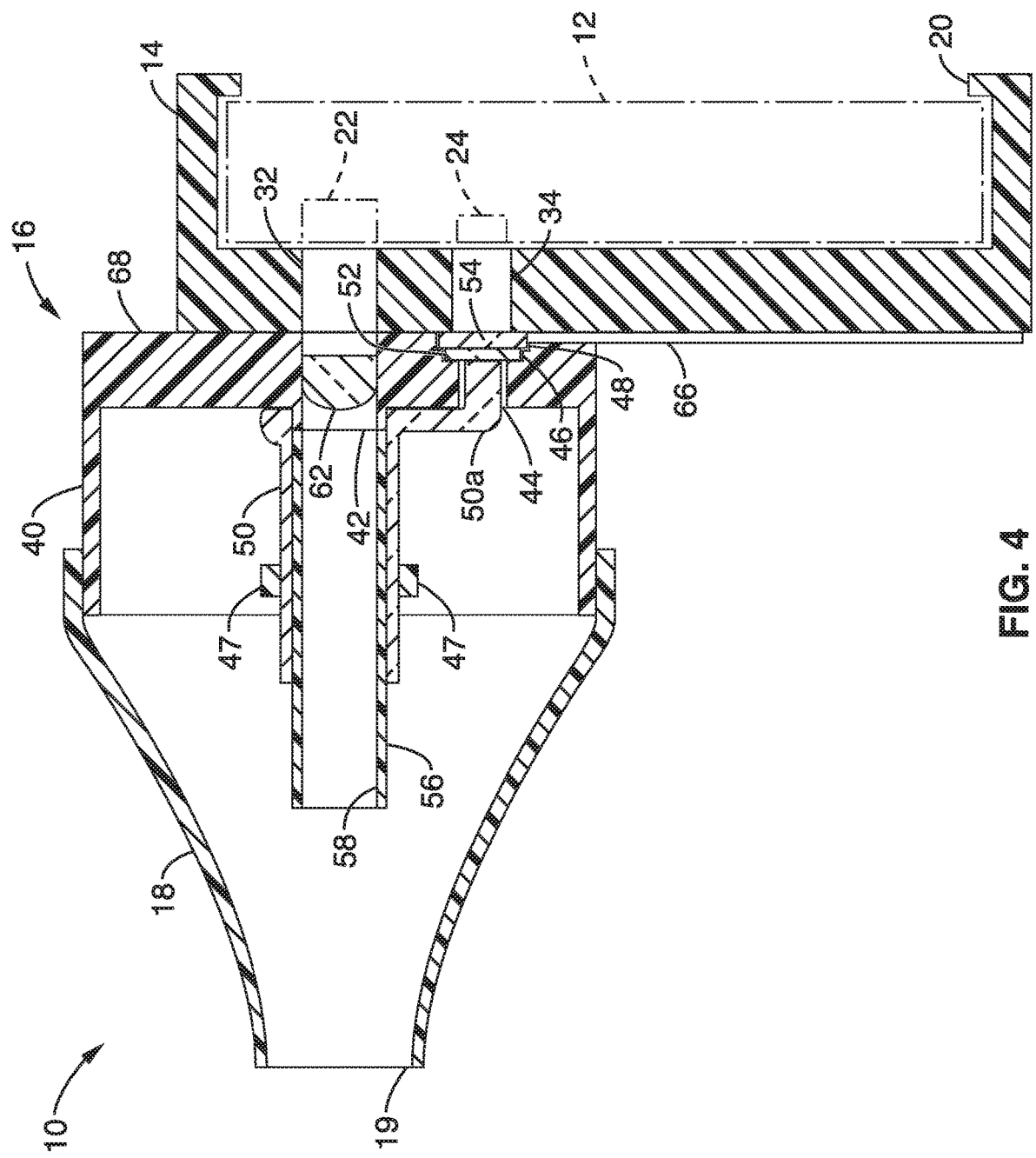
FIG. 4 shows a cross-sectional view of the imaging apparatus of FIG. 1A installed on a mobile device in accordance with the present invention.

FIGS. 1A and 1B show a releasable optical assembly 16 attached to base 14. The releasable optical assembly 16 comprises a cylindrical housing 40 and a conical-shaped speculum 18. Speculum 18 is shown sized and shaped for ear drum imaging as an otoscope. The speculum 18 is one of many different optical attachments that may be used to interface the imaging apparatus 10 with varying anatomical features. In particular, speculum 18 may be sized and shaped for proper interface with various body cavities, including nasal, oral, vaginal, and anal cavities, etc. Speculum 18 is configured for quick release attachment to housing 40. As shown in FIG. 4, the speculum 18 is shown with a contact fit over housing 40. However, other attachment means, e.g. mating threads, clips, snaps, tab-and-grooves, etc., may also be used.

Accordingly, the base member 14 also includes means (not shown) for coupling the releasable optical assembly 16 to the base member 14, such as clip-on, snap-on, slide-on, twist-on, and other conventional means for attachment. For example the releasable optical assembly 16 may have pins that line up with and snap into one or more corresponding slots in the base member, or vise versa.

Figure 2:
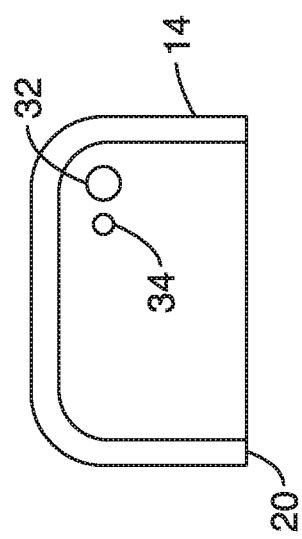
FIG. 2 shows a view of the rear side of the imaging apparatus of FIG. 1A.

FIG. 2 shows a view of the rear side of the imaging apparatus 10 and base 14. Base 14 comprises clip-on walls 20 that help retain the base 14 on to the mobile device 12. The base 14 comprises an illumination port 34 configured to align with the phone's LED flash 24 to allow illuminated light to pass through the case and into the releasable optical assembly 16. The base 14 also comprises and an imaging port 32 allowing line of sight for the phone's camera 22 from the releasable optical assembly 16.

FIG. 3 shows the imaging apparatus 10 installed on a mobile device 12 with outer speculum attachment 18 removed for clarity. An optical tube 56 is centered within the housing opening and has a tube aperture 58 configured to line up with the imaging port 32 of the base 14.

FIG. 4 shows a cross-sectional view of the imaging apparatus 10 installed on mobile device 12. The back wall 68 of the housing 40 comprises an imaging opening 42 that is configured to line up with optical tube 56, imaging port 32 and camera 22. Optical tube 56 may be an integral member with housing 40, or attached to the housing 40. The imaging port 32 and opening 42 provide an optical path for imaging. A lens 62 (or series of lenses) is preferably disposed within the optical tube 56, imaging opening 42 or imaging port 32 (shown in preferred configuration in imaging opening 42). The lens 62 is preferably configured to provide magnification of the target anatomy (e.g. ear drum, etc.). In one embodiment, lens 62 comprises a plano-convex lens with a 48 mm focal length. It is appreciated that lens 62 may comprise any number of differing types, (e.g. bi-convex, convex-meniscus, etc.), or any combination of lenses known in the art.

It is also appreciated that lens 62 may comprise microlens array (e.g. two or more lenses space apart in a planar array) in place of a single lens. Light passes through normal to the 2D array (not shown). Each lens element in the array has a shorter focal length/higher magnification than the larger lenses (e.g., the 48 mm f lens in the otoscope, so the design can be much more compact. Due to the space in between the array elements, the array can be scanned to capture the individual images, which are then assembled into a unified image of the field without gaps. This allows for a high magnification system in a much smaller form factor.

The imaging apparatus 10 preferably comprises means for directing the light from the phone's LED flash 24 to provide improved illumination. Use of just the LED flash 24 to illuminate the anatomical target (e.g. ear drum) directly would lead to shadows from the optical tube 56. Illumination with the fiber optics may be used to eliminate shadows. The light can be directed to provide on-axis illumination, as well as oblique or off-axis illumination for better contrast for some applications.

The back wall 68 of the housing 40 further comprises an illumination opening 44 that is configured to line up with a fiber optic bundle 50a, illumination port 34 and flash 24. Fiber optic bundle 50a generally comprises one or more optical fibers, configured with end glow or side glow characteristics to suit the particular application or anatomy being imaged.

In a preferred embodiment, the fiber optic bundle 50a connects at one end to the illumination opening 44 and wraps and extends to optical tube 56, with optical fibers 50 extending axially around optical tube 56 to form a coaxial layer at least partially surrounding the optical tube. The individual optical fibers 50 preferably form a continuous layer around tube 56. However it is appreciated that the optical fibers may also surround the tube at spaced intervals. Optical fibers 50 extend at least a portion of the length of tube 56 such that the end of the optical fibers are aligned in the direction of the tube 56 axis and preferably near the free end of the tube 56. Optical fibers are held in place on tube 56 via an adhesive, band 47, or like attachment means. The bundle 50a and fibers 50 are configured to propagate light from flash 24 (e.g. LED or the like) and direct it toward the free end of the optical tube 56 and in the direction of speculum 18. The optical fibers 50 arrayed around the end of the tube 56 provide a more uniform ring of illumination in the direction of the target anatomy. Such directed light is particularly useful for viewing/imaging cavities in the body such as the ear or mouth, where light is limited.

The imaging apparatus is configured such that when base member 14 and releasable optical assembly 16 are attached to device 12, all optical apertures (speculum aperture 19, optical tube aperture 58, optical opening 42, and optical port 32) are in substantially concentric alignment with camera 22, and correspondingly, all illumination apertures (illumination opening 44, illumination port 34) are all in substantially concentric alignment with flash 24.

In a preferred embodiment, the optical assembly 16 may also contain one or more filters in the illumination path to improve the illumination of the target anatomy. The filters may be positioned in fixed or adjustable configuration at or between one or more structures of the imaging apparatus 10. A sliding color spectrum filter may also be positioned in the path of the LED flash 24 to enable selective color illumination for spectrophotometric applications.

In one embodiment, the filters may comprise one or more of polarizing filters, neutral density filters, or diffusers, or the like. For example, one or more polarizing filters can be used to reduce glare and/or shadows, in addition to controlling illumination intensity and uniformity. Thus, filters may be used to control the intensity and pattern of illumination based on the phone's LED flash 24 (or an integrated light source as provided in FIG. 12, described in further detail below), and/or to reduce glare for imaging a reflective sample (such as like oily skin). With use of variable filters, the intensity of sample illumination can be adjusted without changing the output provided by the device LED 24. For the iPhone for example, the LED flash 24 is either on or off when no software support for adjustable intensity is provided, making exposure difficult in some applications.

In one example of a tunable illumination system illustrated in FIG. 4, two polarizing filters 52, 54 are stacked in series between the handset LED 24 and the illuminated anatomical target. Referring further to FIG. 7, the first filter 52 is fixed and disposed within a rectangular counter bore 46 set into the rear wall 68 of housing 40. The second filter 54 is set into a circular counter bore 48 in housing 40, and is configured to be rotated with use of lever 66 to modulate the intensity of the light transmitted to the sample anatomy. It is appreciated that the filters 52, 54 may be positioned anywhere within the optical path, e.g. within corresponding counter bores (not shown) in the base 14. The intensity of the transmitted light is controlled by the relative orientation of the filters 52, 54, where parallel orientation permits the maximum transmission and perpendicular orientation permits minimal transmission. This could also be achieved with a gradient neutral density filter, which could be moved (rotated in the case of a circular gradient) to adjust the light transmission A spectral selection tool may also be included for controlling illumination wavelength. A slider (or color wheel, etc., not shown) containing color filters may provide for specific wavelengths to be chosen from the LED 24 illumination. This enables comparison of images taken with different colors to look for absorption differences. This is useful in skin imaging, for example.

The optical assembly 16 may also comprise one or more filters in the optical path (e.g. between optical port 32 and optical opening 42). For example, one or more filters comprising a polarizer, neutral density filter, or spectral selection filter may be positioned in the optical path using a system similar to the illumination filters 52, 54 of FIG. 4.

Optical assembly 16 may further allow for adjustment of the optical components (e.g. lens 62). For example, optical assembly 16 may comprise a lens slider (not shown) similar to slider 66 in FIGS. 4-6 to allow for one or more lenses to be moved in and out of the optical path (lens stacking), or for lens position to be moved along the optical axis. Removing all attachment lenses 62 from the path provides the device's 12 standard imaging characteristics, while adding one or more lenses 62 in the optical path modifies the imaging characteristics to suit the application. Thus, single optical assembly 16 may be configured to provide variable magnification and numerical aperture characteristics, similar to the way that many microscopes contain a turret of objectives.

Figure 5:
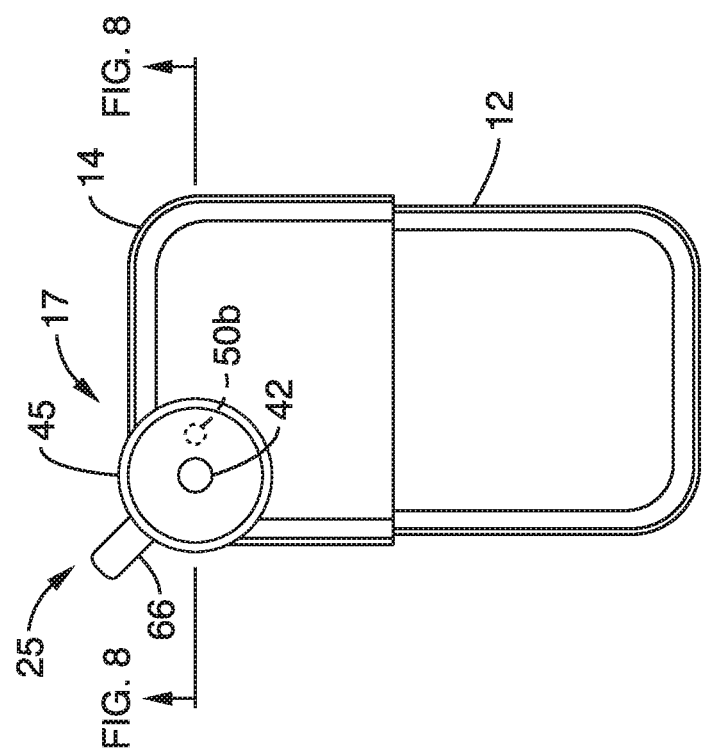
FIG. 5 shows an alternative imaging apparatus in accordance with the present invention.

FIGS. 5-8 show an imaging apparatus 25 preferably configured for use in imaging skin surfaces, and in particular, non-cavity-type skin surfaces. Referring to FIG. 5, imaging apparatus 25 includes a releasable optical assembly 17 attached to base 14. The releasable optical assembly 17 comprises an open ended housing or spacer 45 having an optical opening 42. As shown in further detail in the cross-sectional view of FIG. 8, the optical opening 42 provides an open path to the optical port 32 of base 14 and camera 22 of device 12. Spacer 45 of imaging apparatus 25 provides a set distance between camera 22, lens 62 and the image target. When the imaging apparatus 25 is touched to the image target (skin, hair, etc.) directly, the image target is within the focus range for the camera 22, facilitating image collection. This distance may be adjustable (to discrete distances or continuously) to accommodate different imaging applications. Spacer 45 may also include an additional sliding tube (as provided in tube 96 in calibration tool 90 shown in FIG. 11) to provide adjustable spacing. Thus, the spacer element 45 could be adjusted to discrete or continuous height steps to accommodate the focal length of the lens or lenses 62.

Figure 6:
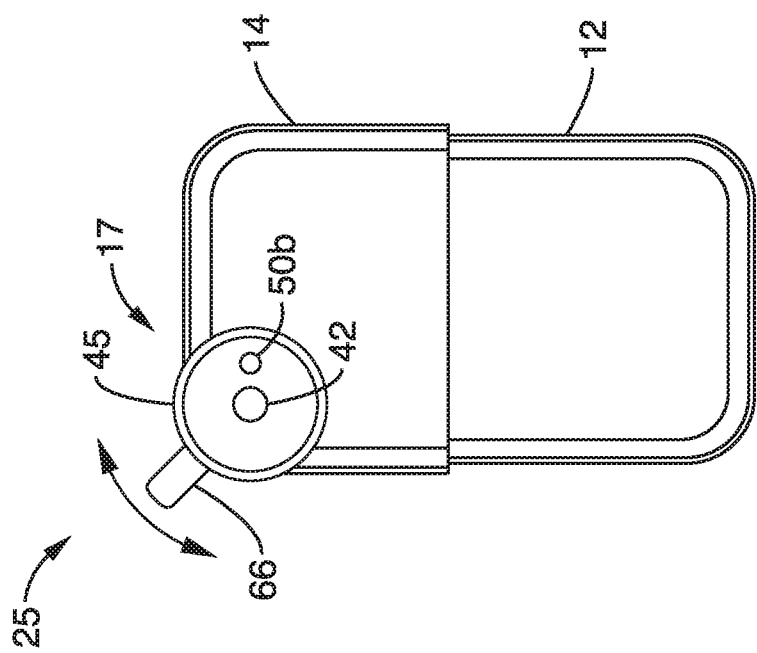
FIG. 6 shows the imaging apparatus of FIG. 5 with the diffuser removed for clarity.

Fiber optic bundle 50b may be used to change the shape and/or position of the light source 24. As shown in FIGS. 5 and 6, fiber optic bundle 50b could be arrayed under a diffuser 60 to provide controlled (e.g. uniform) illumination, (FIG. 6 shows the diffuser removed for clarity). Referring now to the cross-sectional view of FIG. 8, the fiber optic bundle 50b is disposed within illumination opening 44 of the housing 45, such that the fiber optic bundle 50b is in line with illumination port 34 of the base 14 and LED 24 of device 12. Similar to apparatus 16 shown in FIGS. 1-4, and 7, the optical attachment assembly 17 may also comprise filters 52, 54, and slider handle 66 in addition to bores 46 and 48 in the housing 45 to provide additional illumination filtering.

FIG. 9 shows the imaging apparatus 27 similar to imaging apparatus 25 of FIGS. 5-6, with calibration module 70 disposed on spaced 45. Calibration module 70 comprises a test pattern feature 72 which appears in a portion of the image field of view to enable calibration of color, white balance, exposure, and size. In one embodiment, black, white, grey and color patches with known color values on the calibration pattern serve as a reference for post-processing of the image. The test pattern also provides an exposure reference (based on the appearance of the black patches in the image) and a size scale due to the known size of the pattern elements. The calibration module 70 is instrumental in controlling imaging from a device 12, such as a mobile phone, which was not designed to produce absolute color/exposure references. Preferably, the calibration module 70 is integrated into the imaging apparatus 27. It is also appreciated that calibration module 70 may be disposed within aperture 19 of disposable speculum 18 for calibrating device 10.

Alternatively, a reference feature may be used as an external test pattern or a common object (for example, a coin). Including a known object in the field of view enables size and color calibration of the resulting image, especially when its depth position is known or can be determined from the image. A coin held next to the earlobe can be used by software to determine (or reasonably estimate) the absolute size of the facial features.

FIGS. 10A through 11 illustrate focus and illumination tools for pre-capture calibration to pre-set the exposure and focus before capturing an image.

FIGS. 10A and 10B show perspective and plan views, respectively, of an exposure calibration tool 80 according to the present invention. In the otoscope application, for example, the camera's 22 exposure setting may use a larger region of interest (ROI) than the actual image region at the end of the tip of speculum 18. In that case it is useful to set the exposure relative to a brighter image in the smaller field at the end of the tip, to compensate for the mismatch with the camera's 12 ROI. Exposure calibration tool 80 comprises a stepped platform 82 a distance h from a lower platform 84. The stepped platform 82 has large 86 and small 88 dark apertures, and the lower platform 84 correspondingly comprises large 76 and small 78 lighter apertures. Exposure calibration is performed by inserting imaging apparatus 10, 25 (e.g. otoscope tip 18) at the particular apertures 76, 78, 86, 88. The stepped platform 82 provides a sharp image at a known distance to pre-set focus, the lower platform 84 is bright (e.g. with matte aluminum foil or like material, or adjustable to material with a range of known reflectance values) to pre-set the exposure.

It is also useful to preset the focus so that the camera 22 is focused on a known distance before imaging a delicate area of anatomy, such as a patient's eardrum. FIG. 11 shows a perspective view of a focus calibration tool 90 having a base 92 and sliding tube 96 disposed within base tube 94. The sliding tube adjusts to various heights H by sliding within base tube height to allow for a range of focal distance pre-sets. The calibration tool comprises an illumination opening 95 and imaging aperture 98.

The tools 80 and 90 to calibrate focus and exposure may be a separate parts (as shown in FIGS. 10A through 11) or integrated within the imaging device (e.g. calibration module 70 in device 27 FIG. 9). The calibration tool may be adjustable to allow for a range of focal distances (as shown), or use a color wheel or other means to adjust the exposure calibration area FIGS. 12A through 13 illustrate different attachment means according to the present invention.

FIG. 12 A illustrates a side view attachment means coupling an imaging apparatus 104 via manually positioning and affixing the imaging apparatus 104 with a ring 108 (which may be replaceable). Ring 108 may comprise adhesive tape, hook-and-loop closure or magnet to releasably attach to the phone.

FIG. 12B illustrates a plan view of an alternative embodiment for coupling assembly 100. Coupling assembly 100 comprises spring-loaded pincher attachment 102 that is configured to be slideably positioned in the vertical direction. Coupling assembly 100 further comprises a rectangular slot 106 that allows the imaging assembly 104 to be adjusted in the horizontal direction to coincide with the phone 12 camera 22 and flash 24.

FIG. 13 illustrates modular imaging system 120 comprising separated components for imaging and illumination. The flexible fiber bundle 124 is attached to the optical cone 122, such that the fiber bundle 124 can be bent to accommodate a variety of camera 22 and LED/flash 24 positions on the mobile device 12 or case 14 provided with the device. The system 120 is shown in the otoscope-type configuration 10 of FIGS. 1-4, with a cone 122 to which disposable specula can be attached. The same modular approach may also be applied to the apparatus 25 of FIGS. 5-6.

FIG. 14 shows a modular attachment system 150 having independent light source 162. System 150 may comprise a disposable speculum 152 that tapers toward its tapered free end, and having tabs 164 at its proximal end for attachment to slot 166 in housing 168. A separate attachment cone 154 may also be included, and have slot 166 for attaching to housing 168. An optical tube 156 containing one or more lenses 62 is provided within housing 168, and is wrapped in fiber optics 158 for illumination. The fiber bundle 158 can draw light from the phone's LED flash 24, an external light source 162 by means of elongate tube 160.

The image enhancement systems shown in FIGS. 1-14 may be used not only for capturing enhanced digital images and video, but also as a real-time scope for viewing patient anatomy. For example, one could be treating the integrated mobile device 12 as an otoscope for display on the mobile device's screen. At any time, an image capture or video may also be initiated to store the image or video in memory, and transmit the image or video if necessary.

Figure 15:
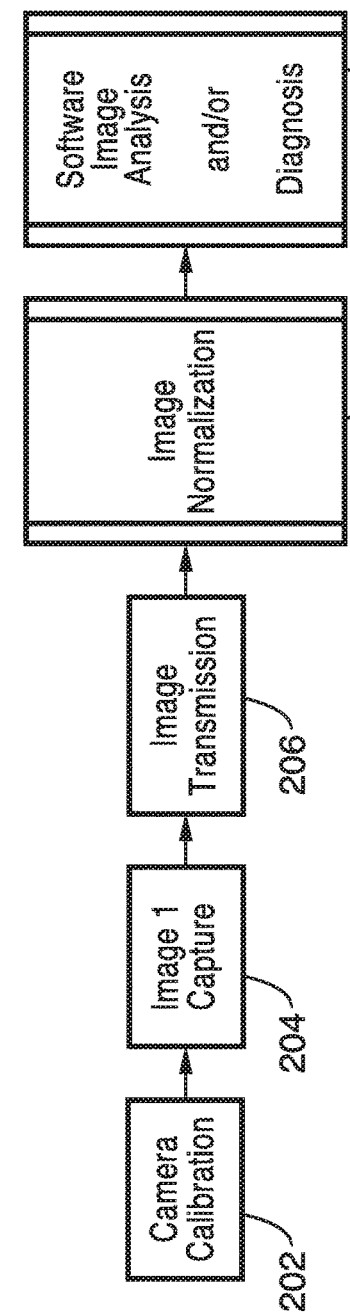
FIG. 15 shows a method for two-way optical data transmission from a mobile device according to the present invention.
Figure 16:
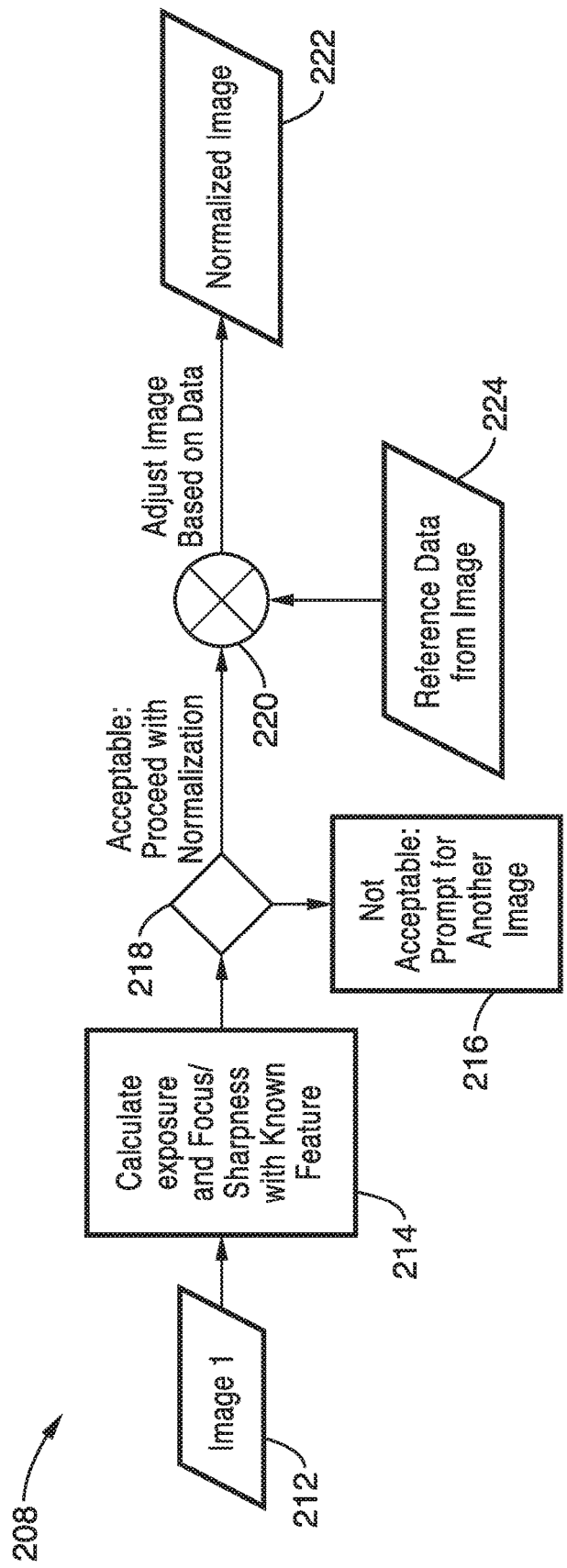
FIG. 16 shows a flow diagram of the image normalization step of FIG. 15.
Figure 17:
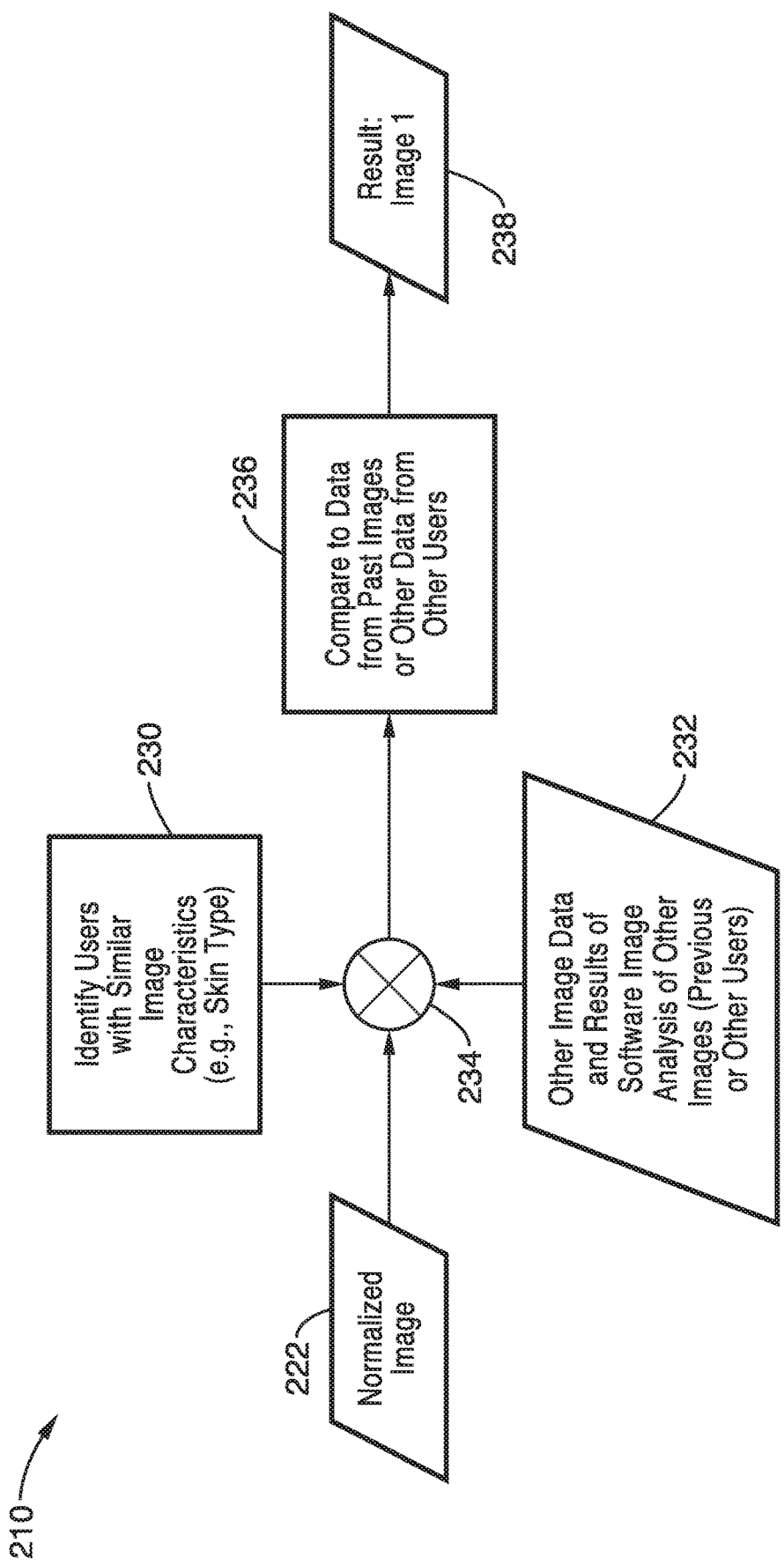
FIG. 17 shows a flow diagram of the image analysis step of FIG. 15.

FIGS. 15 through 17 illustrate a system and method for post processing an image captured from a mobile device 12. While it is preferred that software for carrying out method 200 be used in conjunction with the image enhancement apparatus disclosed in FIGS. 1 through 14, it is appreciated that the methods disclosed in FIGS. 15 through 17 may be used for any mobile device, webcam, or camera directly, with or without the image enhancement apparatus disclosed in FIGS. 1 through 14. Accordingly, a preferred embodiment of the present invention is a system comprising one or more of the enhancement apparatus disclosed in FIGS. 1 through 14, along with software using methods and algorithms embodied in FIGS. 15 through 17.

FIG. 15 shows a method 200 for two-way optical data transmission from a mobile device, which allows the user to point the imaging apparatus 10, 25 at a surface, while displaying the real-time image of the surface on a secondary device, such as a computer. The secondary device can control the features of the imaging system 10, 25, such as choosing the focus region of interest, exposure, and image collection, etc. Method 200 may be implemented within a software module or application for execution on a processor of the wireless device, as well as applications for execution on the secondary device such as a computer.

As shown in FIG. 15, a first step in the method 200 is calibration of the camera 22 at block 202. Next an image is captured at block 204 and transmitted to secondary device at block 206. Image normalization is then performed at block 208, and image analysis and/or diagnosis is performed at step 210. Captured images may be transmitted for analysis by software algorithms or a person for a range of applications including diagnosis, monitoring and product recommendations.

While image transmission step 206 may be desirable to perform calculation intensive tasks such as image normalization step 208 and image analysis/diagnosis step 210 on a computer or other device configured to quickly perform such calculations, it will be appreciated that transmission step 206 is optional, and that one or both of the image normalization step 208 and image analysis/diagnosis step 210 may be performed using software and programming on the mobile device 12.

FIG. 16 illustrates in further detail the image normalization step 208 of method 200. First, exposure and focus sharpness of image 212 is calculated with a known feature at step 214. If the calculation returns non-acceptable results at evaluation step 218, the device 12 is prompted for another image to be captured at step 216. If the calculation returns acceptable results at evaluation step 218, the reference data from image 212 is used at step 220. The image is then adjusted at step 220 to generate the normalized image 222.

Image normalization step 208 has the capability to normalize the image based on test pattern portion of the image 212 as an application loaded as either on-board software on the mobile device 12, or by uploading the image 212 for server-side processing. The normalization step 208, which may comprise white balance, exposure, focus, etc., may be based on the imaging apparatus 10 integrated test pattern (e.g. calibration module 70), or on another known standard.

The orientation of the image 212 may also be adjusted in step 210 using reference features in the image 212 (e.g. in the case of ear drum imaging, adjusting the rotation of the image based on the "cone of light" feature of the ear drum), or using on-board sensors within device 12 such as the accelerometer or gyroscope. This is a significant advantage in ear drum imaging, for example, where the doctor is used to a certain orientation but the imaging device may produce a rotated view. Normalization step 208 can identify corresponding features from two images to determine whether they have overlapping areas. This too can be improved by adding in accelerometer/gyroscope data, so that the overlap detection is based on images with the same orientation (this compensates for a rotation difference between the two images).

Normalization data may also be used to override the camera 22 automatic focus and exposure settings so as not to interfere with the acquired calibrated settings.

FIG. 17 illustrates in further detail the image analysis and/or diagnosis step 210 of method 200. Diagnosis step 210 provides image processing (either via executing an application on-board the phone/device 12 or uploaded for server-side processing) to analyze images for features of interest, such as skin image analysis for wrinkles, lines, redness, blood vessels, dryness, coloration, UV damage and roughness. At step 234, the normalized image 222, similar image characteristics (e.g. skin type) identified from other users 230 and other image data and results from image analysis or other users are input. Data from 230 and 232 may comprise a database of images and associated data. At step 236 the normalized data 222 is compared with data from past images or other user data to arrive at resulting image 238.

Software loaded on the mobile device 12 or secondary device may use the results 238 of image analysis to provide recommendations and/or targeted ads to user. In the case of skin care, image analysis provides data on skin type and condition (e.g. Fitzpatrick type, oily/dry/combination, UV damage, wrinkles, etc) and the user is provided with targeted product recommendations. The software also allows users to track images over time to monitor changes, results of product usage, etc. Recommendations and ads can be based on aggregated data from users from a similar class (e.g. with similar skin types). For example, image analysis (from the magnified imaging system 10, 25 of the present invention, or standard cameras) may be used to show that users with similar skin have recorded better results using a particular product.

For skin imaging of the face, which can be difficult to self-take, the method 200 and associated software have the capability to transmit the image in real time for display on the secondary device (e.g., another phone or computer via the device application or website). The communication can be two-way, so that the imaging system functions (focus, exposure, image capture, etc.) can be controlled from the second device.

Images 204 may be tagged with GPS and/or time/date stamp information, which can be used to authenticate the user or perform geographical meta-analysis of results.

Video may also be captured by on the device 12, and analyzed by method 200 using software on the device or server-side to identify key frames or to generate an enhanced single frame. For example, in the ear exam application, the software may identify the best frame to present to the physician by using a standard sharpness detection algorithm to find the frame with the sharpest cone of light (bright reflection off the ear drum with a defined border). This video could be taken while moving the device around, or while adjusting the focal distance (such as running the camera's 12 autofocus function). Video during autofocus provides a set of frames that are focused on a series of focal distance planes. This may then be used to identify the best frame, or to provide something analogous to the 3D image reconstruction done with a confocal microscope image stack.

It is also appreciated that the optical enhancement systems of FIGS. 1-14 and image processing methods of FIGS. 15-17 may also be useful with 3D stereo cameras now available on some phones). Stereo images may be used help in skin imaging, for example to measure the depth of wrinkles or the height of a mole.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. An imaging apparatus for a portable wireless device having a built-in camera, comprising: a releasable optical assembly, comprising: a housing; the housing comprising an attachment surface for releasably coupling the releasable optical assembly to the portable wireless device; and an optical transmission element; wherein the optical transmission element is configured to enhance an image taken by the built-in camera prior to the image being received the portable wireless device.

2. The apparatus of embodiment 1, wherein the optical transmission element comprises a first optical transmission element configured to magnify the image.

3. The apparatus of embodiment 2, wherein the optical transmission element comprises a second optical transmission element configured to enhance illumination of the image.

4. The apparatus of embodiment 3: wherein the first optical transmission element comprises a lens; the housing configured to house the lens in an alignment within an optical path of the built-in camera.

5. The apparatus of embodiment 4: the portable wireless device further comprising an illumination source; wherein the second optical transmission element comprises an optical fiber; the housing configured to house the optical fiber in an alignment within the illumination path of the illumination source; and wherein the optical fiber is configured to alter the illumination path to enhance illumination of the image.

6. The apparatus of embodiment 5: the releasable optical assembly further comprising one or more optical filters coupled to the housing; and the housing configured to house the one or more optical filters in an alignment within the one or more of the illumination path or optical path.

7. The apparatus of embodiment 6, wherein the one or more optical filters comprises a filter comprising one or more of a: polarizer, neutral density filter, or spectral selection filter.

8. The apparatus of embodiment 6, wherein the one or more optical filters comprises: a first filter having a fixed orientation; a second filter having a variable orientation to allow for adjustment of transmission of light; wherein the first and second filters are stacked in series in one or more of the illumination path and optical path.

9. The apparatus of embodiment 5: wherein the housing further comprises an optical tube; the optical tube having a central aperture; the optical tube being attached to the housing such that the central aperture is aligned with the optical path when the releasable optical assembly is attached to the portable wireless device; wherein the optical tube comprises a free end extending away from the housing and built-in-camera; wherein the optical fiber comprises one of a bundle of optical fibers; the bundle of optical fibers extending from a location at or near the illumination source to the optical tube wherein the optical fibers extend axially along the optical tube toward the free end of the tube to form a coaxial layer at least partially surrounding the optical tube; and wherein the optical fibers are configured to propagate light from the illumination source in the direction of the free end of the optical tube.

10. The apparatus of embodiment 9, further comprising: a speculum configured to interface with a body cavity of a patient; the speculum having a proximal end and distal free end; said speculum comprising a conical shape that tapers from the proximal end to the free end; the proximal end of the speculum configured to releasably attach to the housing; said distal end of the speculum having an aperture configured to concentrically align with the optical tube when the speculum is attached to the housing.

11. The apparatus of embodiment 5: wherein the housing comprises a cylindrical tube having a proximal end comprising the attachment surface; the cylindrical tube having an open distal end extending away from said portable wireless device when the imaging apparatus is attached to said portable wireless device; wherein the cylindrical tube has a predetermined length corresponding to an optical characteristic of said lens and said built in camera; and wherein the open distal end of the cylindrical body is configured to be positioned to contact a surface of a patient's skin to facilitate imaging of said skin surface.

12. The apparatus of embodiment 11: wherein the optical fiber comprises one of a bundle of optical fibers; further comprising a diffuser disposed between the optical fibers and the open distal end of the cylindrical tube; and wherein the diffuser is configured to diffuse light propagated through the bundle of optical fibers.

13. The apparatus of embodiment 5, further comprising: a calibration module attached to said housing; the calibration module being disposed in a field of view of the optical path to provide calibration of the built in camera.

14. The apparatus of embodiment 1, further comprising: a base member; wherein the base member comprises an attachment surface for coupling the base member to the wireless device; wherein the base member is configured to releasably attach to the housing; and wherein the base member comprises at least one aperture aligned with the illumination path and optical path for imaging and illumination through the housing.

15. A system for enhancing and post-processing images obtained from a portable wireless device having a built-in camera, comprising: a releasable optical assembly, comprising: a housing; the housing comprising an attachment surface for releasably coupling the releasable optical assembly to the portable wireless device; an optical transmission element; wherein the optical transmission element is configured to enhance an image taken by the built-in camera prior to the image being received the portable wireless device; programming executable on said wireless device or other external device for: receiving the enhanced image; post processing the enhanced image.

16. The system of embodiment 15, wherein post processing comprises image normalization.

17. The system of embodiment 16, wherein image normalization comprises: calculating one or more of exposure and focus characteristics with a known feature; and adjusting the image based on reference data from the image.

18. The system of embodiment 16, wherein said programming is further configured for calibrating said built in camera as a function of optical characteristics releasable optical assembly.

19. The system of embodiment 17, wherein said programming is further configured for: inputting data from the normalized image along with other image data; and comparing the data from the normalized image with the other image data to analyze said image.

20. The system of embodiment 19, wherein the other image data comprises images from similar images to the normalized image.

21. The system of embodiment 20, wherein the normalized image comprises an image of a person's skin; and wherein the other image data comprises skin images from patients having similar skin characteristics.

22. The system of embodiment 19, wherein said programming is further configured for: transmitting said image to a secondary device to perform post processing.

23. The system of embodiment 15, wherein the optical transmission element comprises a first optical transmission element configured to magnify the image and a second optical transmission element configured to enhance illumination of the image.

24. The system of embodiment 23: wherein the first optical transmission element comprises a lens; the housing configured to house the lens in an alignment within an optical path of the built-in camera; the portable wireless device further comprising an illumination source; wherein the second optical transmission element comprises an optical fiber; the housing configured to house the optical fiber in an alignment within the illumination path of the illumination source; and wherein the optical fiber is configured to alter the illumination path to enhance illumination of the image.

25. The system of embodiment 24: the releasable optical assembly further comprising one or more optical filters coupled to the housing; and the housing configured to house the one or more optical filters in an alignment within the one or more of the illumination path or optical path.

26. The system of embodiment 25, wherein the one or more optical filters comprises a filter comprising one or more of a: polarizer, neutral density filter, or spectral selection filter.

27. The system of embodiment 24: wherein the housing further comprises an optical tube; the optical tube having a central aperture; the optical tube being attached to the housing such that the central aperture is aligned with the optical path when the releasable optical assembly is attached to the portable wireless device; wherein the optical tube comprises a free end extending away from the housing and built-in-camera; wherein the optical fiber comprises one of a bundle of optical fibers; the bundle of optical fibers extending from a location at or near the illumination source to the optical tube wherein the optical fibers extend axially along the optical tube toward the free end of the tube to form a coaxial layer at least partially surrounding the optical tube; and wherein the optical fibers are configured to propagate light from the illumination source in the direction of the free end of the optical tube.

28. The system of embodiment 27, further comprising: a speculum configured to interface with a body cavity of a patient; the speculum having a proximal end and distal free end; said speculum comprising a conical shape that tapers from the proximal end to the free end; the proximal end of the speculum configured to releasably attach to the housing; said distal end of the speculum having an aperture configured to concentrically align with the optical tube when the speculum is attached to the housing.

29. The system of embodiment 24: wherein the housing comprises a cylindrical tube having a proximal end comprising the attachment surface; the cylindrical tube having an open distal end extending away from said portable wireless device when the imaging apparatus is attached to said portable wireless device; wherein the cylindrical tube has a predetermined length corresponding to an optical characteristic of said lens and said built in camera; and wherein the open distal end of the cylindrical body is configured to be positioned to contact a surface of a patient's skin to facilitate imaging of said skin surface.

30. A method for enhancing and post-processing images obtained from a portable wireless device having a built-in camera, comprising: receiving an image from a built-in camera of a portable wireless device; wherein the portable wireless device comprises a releasable optical assembly releasably disposed within a field of view of the built-in camera; wherein the releasable optical assembly comprises an optical transmission element configured to enhance the image prior to the image being received by the portable wireless device; and post processing the enhanced image.

31. The method of embodiment 30, further comprising: transmitting the enhanced image to a secondary device for post processing.

32. The method of embodiment 30, wherein post processing comprises normalizing the image.

33. The method of embodiment 32, wherein normalizing the image comprises: calculating one or more of exposure and focus characteristics with a known feature; and adjusting the image based on reference data from the image.

34. The method of embodiment 30, further comprising: calibrating said built in camera as a function of optical characteristics releasable optical assembly.

35. The method of embodiment 33, further comprising: inputting data from the normalized image along with other image data; and comparing the data from the normalized image with the other image data to analyze said image.

36. The method of embodiment 35, wherein the other image data comprises images from similar images to the normalized image.

37. The method of embodiment 35, wherein the normalized image comprises an image of a person's skin; and wherein the other image data comprises skin images from patients having similar skin characteristics.

38. The method of embodiment 30, wherein the optical transmission element comprises a first optical transmission element configured to magnify the image and a second optical transmission element configured to enhance illumination of the image. Although the description above contains many details, these should not be construed as limiting the scope of the invention but as merely providing illustrations of some of the presently preferred embodiments of this invention.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method for enhancing and post-processing images obtained from a portable wireless device having a built-in camera comprising one or more device lenses and an image sensor, the method comprising:

coupling a releasable optical assembly to the portable wireless device such that the releasable optical assembly is disposed within a field of view of the built-in camera;

receiving an input image with the built-in camera of the portable wireless device;

wherein the releasable optical assembly comprises an optical transmission element in alignment with the image sensor of the camera such that the input image is enhanced and projected onto the image sensor using a combination of the optical transmission element and the one or more device lenses of the portable wireless device; and post processing the enhanced image;

wherein said post processing comprises:

(i) calculating one or more of exposure and focus characteristics of the enhanced image with a known feature and evaluating the enhanced image for acceptability; and (ii) if the enhanced image is acceptable based on step (i), normalizing the enhanced image for one or more of color levels, exposure, and orientation based on reference data related to the enhanced image.

2. A method as recited in claim 1, further comprising: transmitting the enhanced image to a secondary device for post processing.

3. A method as recited in claim 1, further comprising: calibrating said built in camera as a function of optical characteristics releasable optical assembly.

4. A method as recited in claim 1, further comprising: inputting data from the normalized image along with other image data; and comparing the data from the normalized image with the other image data to analyze said normalized image.

5. A method as recited in claim 4, wherein the other image data comprises images from similar images to the normalized image.

6. A method as recited in claim 4;

wherein the normalized image comprises an image of a person's skin; and wherein the other image data comprises skin images from patients having similar skin characteristics.

7. A method as recited in claim 1, wherein the optical transmission element comprises a first optical transmission element configured to magnify the input image and a second optical transmission element configured to enhance illumination of the input image.

8. A method for enhancing and post-processing images obtained from a portable wireless device having a built-in camera comprising one or more device lenses and an image sensor, the method comprising:

(a) coupling a releasable optical assembly to the portable wireless device such that the releasable optical assembly is disposed within a field of view of the built-in camera;

(b) receiving an input image with the built-in camera of the portable wireless device;

(c) wherein the releasable optical assembly comprises an optical transmission element in alignment with the image sensor of the camera such that the input image is enhanced and projected onto the image sensor using a combination of the optical transmission element and the one or more device lenses of the portable wireless device;

(d) post processing the enhanced image; and (e) transmitting the enhanced image to a secondary device for post processing;

(f) wherein post processing comprises normalizing the enhanced image; and
(g) wherein normalizing the enhanced image comprises:
(i) calculating one or more of exposure and focus characteristics of the enhanced image with a known feature and evaluating the enhanced image for acceptability; and
(ii) if the enhanced image is acceptable based on step (g)(i), adjusting the enhanced image for one or more of color levels, exposure, and orientation based on reference data related to the enhanced image.

9. A method as recited in claim 8, further comprising:
calibrating said built in camera as a function of optical characteristics releasable optical assembly.

10. A method as recited in claim 8, further comprising:
inputting data from the normalized image along with other image data; and
comparing the data from the normalized image with the other image data to analyze said image.

11. A method as recited in claim 10, wherein the other image data comprises images from similar images to the normalized image.

12. A method as recited in claim 10:
wherein the normalized image comprises an image of a person's skin; and
wherein the other image data comprises skin images from patients having similar skin characteristics.

13. A method as recited in claim 8, wherein the optical transmission element comprises a first optical transmission element configured to magnify the input image and a second optical transmission element configured to enhance illumination of the input image.

14. A method for enhancing and post-processing images obtained from a portable wireless device having a built-in camera comprising one or more device lenses and an image sensor, the method comprising:
(a) coupling a releasable optical assembly to the portable wireless device such that the releasable optical assembly is disposed within a field of view of the built-in camera;
(b) receiving an input image with the built-in camera of the portable wireless device;
(c) wherein the releasable optical assembly comprises an optical transmission element in alignment with the image sensor of the camera such that the input image is enhanced and projected onto the image sensor using a combination of the optical transmission element and the one or more device lenses of the portable wireless device;
(d) post processing the enhanced image;
(e) transmitting the enhanced image to a secondary device for post processing;
(f) wherein post processing comprises normalizing the image by calculating one or more of exposure and focus characteristics of the enhanced image with a known feature, evaluating the enhanced image for acceptability, and if the enhanced image is acceptable, normalizing the image for one or more of color levels, exposure, and orientation based on reference data from related to the enhanced image;
(g) calibrating said built in camera as a function of optical characteristics releasable optical assembly;
(h) inputting data from the normalized image along with other image data; and
comparing the data from the normalized image with the other image data to analyze said image;
(j) wherein the other image data comprises images from similar images to the normalized image;
(k) wherein the normalized image comprises an image of a person's skin; and
(l) wherein the other image data comprises skin images from patients having similar skin characteristics.

15. A method as recited in claim 14, wherein the optical transmission element comprises a first optical transmission element configured to magnify the input image and a second optical transmission element configured to enhance illumination of the input image.

* * * * *